United States Patent [19]

Kaufman

[11] 4,308,587
[45] Dec. 29, 1981

[54] APPARATUS FOR DISPLAYING AT LEAST TWO PARAMETERS OF POPULATIONS OF PARTICLES ON A CATHODE RAY TUBE

[75] Inventor: Marc T. Kaufman, Los Altos Hills, Calif.

[73] Assignee: Becton Dickinson and Company, Rutherford, N.J.

[21] Appl. No.: 106,726

[22] Filed: Dec. 26, 1979

[51] Int. Cl.³ .................. G01N 15/00; G06F 3/153
[52] U.S. Cl. .................. 364/555; 358/107; 364/521
[58] Field of Search .......... 364/521, 555; 358/107, 358/903

[56] References Cited

U.S. PATENT DOCUMENTS

| | | | |
|---|---|---|---|
| 3,320,409 | 5/1967 | Larrowe | 364/521 X |
| 3,952,297 | 4/1976 | Stauffer et al. | 364/521 X |
| 4,027,148 | 5/1977 | Rosenthal | 364/521 X |
| 4,032,760 | 6/1977 | Quarton et al. | 364/521 |
| 4,115,694 | 9/1978 | Lange et al. | 364/521 X |
| 4,115,806 | 9/1978 | Morton | 358/107 |

FOREIGN PATENT DOCUMENTS 134895  3/1978  Fed. German Demo. Rep...364/521

Primary Examiner—Felix D. Gruber
Attorney, Agent, or Firm—Flehr, Hohbach, Test, Albritton & Herbert

[57] ABSTRACT

Apparatus for displaying dots on a cathode ray tube representing populations of particles being analyzed, which includes a pair of digital memories which concurrently store X-Y data pairs for several particles and which drive the X-Y deflection circuits of an associated CRT.

4 Claims, 3 Drawing Figures

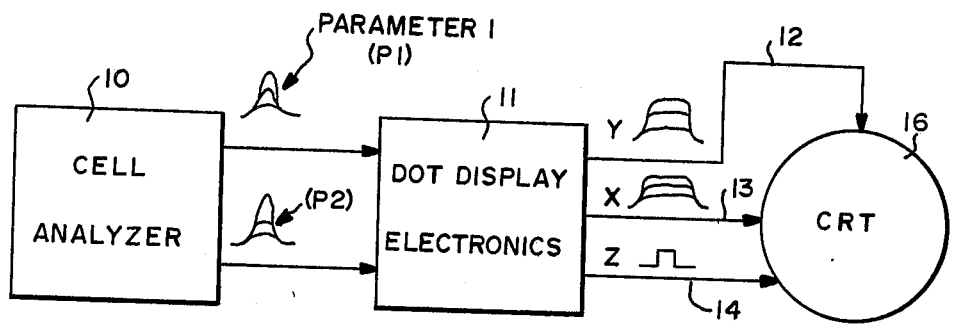
FIG.—1
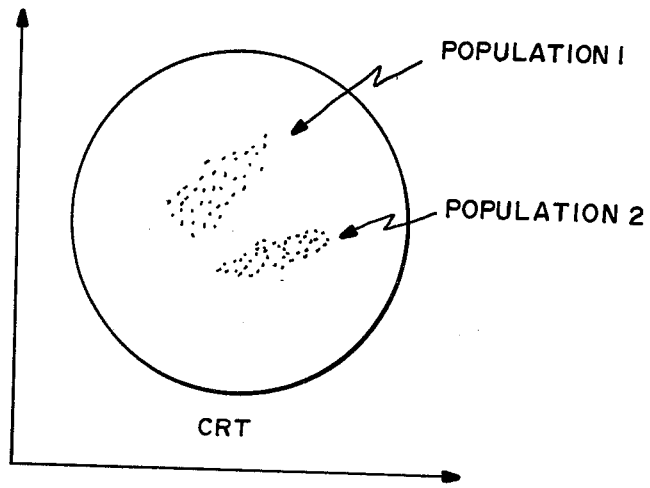
FIG.—2

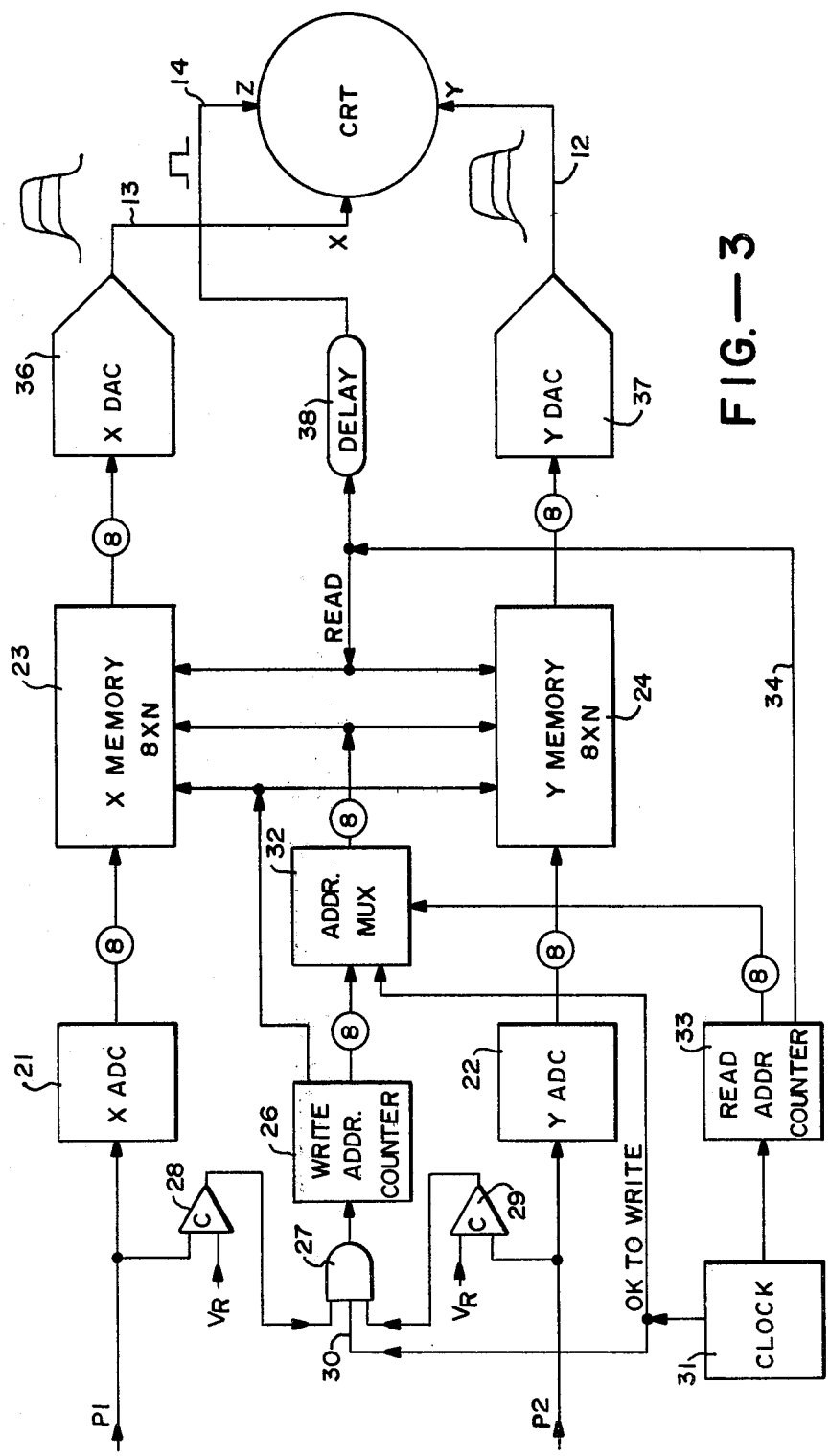
FIG.—3

APPARATUS FOR DISPLAYING AT LEAST TWO PARAMETERS OF POPULATIONS OF PARTICLES ON A CATHODE RAY TUBE

The present invention is directed to apparatus for displaying at least two parameters of populations of particles on a cathode ray tube and more specifically to apparatus which is used in conjunction with a cell analyzer or sorter.

In order to visualize a two-parameter pulse amplitude distribution, such as one generated by a cell analyzer or cell sorter (such as sold by the assignee of the present application under the trademark FACS) a system known as "Dot Display" is often used. The specific display unit has typically been a storage type cathode ray tube (CRT) which retains the individual events or dots on its face from the time they are written until the screen is erased by external control. Alternatively, a long persistence CRT has been used. Each dot of the display represents a correlated measure of two properties of a single cell or particle in a suspension of cells or particles. Each dot is located by X-Y deflection voltages which of course respond to the two properties or parameters of a particle being measured such as for example fluorescence and the amount of light scattered which may relate to the size of the particle.

Although a storage type display has the advantage of allowing a population to be built up and visualized from data which occurs at a very low rate, there are several disadvantages. First, the display has a very limited dynamic range. Once a dot is written at a point on the CRT, it is displayed in full intensity until erased. Subsequent dots at the same location will not increase the perceived intensity at that location. Additionally, if the display is allowed to operate for a long enough period, it will ultimately "fill-up" since infrequently occurring X-Y signal pairs will be stored with the same weight as the main population. Finally, storage CRT's are significantly more expensive than conventional CRT's, and can be permanently damaged if the display is allowed to remain on the phosphor for a long period of time.

Variable persistence CRT displays have been proposed but these are very expensive even relative to a storage CRT. Another disadvantage is that persistence is in terms of time rather than in terms of data rate as is the subject apparatus.

Finally, conventional CRT's have been used, but only in case where the data input rate is quite high. Here, the persistence of the CRT-phosphor and the inherent integration of the viewer's eye cause the dot-populations to appear. However, use of a conventional CRT display instead of a special storage tube has been proposed and actually commercially used in spectrum analysis of low frequency signals; for example, the Hewlett-Packard 3580 analyzer. This system is discussed in an article which appeared in *Electronics Magazine,* June 21, 1973, page 116, by Weibel and Whatley. Here, a random access memory is used to store a Y-axis digital number representative of the magnitude of a particular frequency, and the X-axis is a ramp type time base. The system is of course related only to spectrum analysis which is one-dimensional in nature as opposed to dot populations which are two dimensional.

It is therefore an object of the present invention to provide improved apparatus for displaying on a cathode ray tube two parameters of populations of particles.

In accordance with the above object, there is provided an apparatus for displaying on a CRT with X-Y deflection circuits, two parameters of populations of particles. These particles are sorted or analyzed by apparatus which provides for each particle, a pair of substantially concurrent analog signals representative of two properties of each particle of said populations. Analog to digital converter means convert each of the analog signals to a digital number, and a pair of digital storage means, each with a predetermined amount of addressable storage locations, which sequentially store the digital numbers. Previously stored digital numbers are overwritten, i.e. erased and replaced with new data, in the sequence in which stored when the storage is exceeded. Means for reading the pair of storage means includes a pair of digital-to-analog converters for respectively receiving said stored digital numbers and driving the X-Y deflection circuit of the CRT.

FIG. 1 is a block diagram embodying the present invention.

FIG. 2 illustrates a typical display produced by the present invention; and

FIG. 3 is a more detailed diagram of a portion of FIG. 1.

FIG. 1 illustrates in general the system of the present invention, which is used in conjunction with a cell analyzer 10, such as the above mentioned FACS system of the assignee of the present application. There, a stream of cells or particles in a suspension flow past a measuring station to produce the pulse pairs indicated as P1 and P2. These are substantially concurrently produced for each particle to represent a correlated measure of two properties of a single cell. As discussed above, this might be fluoresence and cell size. Dot display electronics 11 process these two analog signals to produce on lines 12 and 13 X and Y analog deflection signals and on line 14 a Z unblanking signal which drives the CRT 16. In the present invention, this is a conventional, non-variable persistence non-storage CRT.

FIG. 2 illustrates a typical display of the CRT where two populations of particles might appear such as populations 1 and 2. These are used by the researcher to graphically analyze the cell sorting data which is also of course permanently recorded elsewhere. But more importantly the on-line graphic display of the data as it is being received, besides aiding in the later interpretation of recorded data, also is a valuable indication of whether or not the experiment is proceeding successfully. For example, by the adjustment of some parameter in the cell analyzer itself, much better data might be produced. Also malfunctions are immediately apparent.

FIG. 3 illustrates the detailed circuitry of the dot display electronics 11 of FIG. 1 and receives the pulse pairs P1 and P2 where they are digitized by X and Y analog-to-digital converters (ADC) 21 and 22. Each converter produces a digital number corresponding to its analog signal input and stores it in respective digital memories 23 and 24. These numbers are sequentially written in the memory by means of a write-address counter 26 which sequentially writes addresses, to sequentially assign a successive event or number to the next higher address. When the last or Nth address has been written into, the next event pair amplitude is written into the lowest address, overriding the previous contents. This process continues for as long as the analog pulse pairs sequentially appear at the ADC inputs. Write-address counter 26 is driven by an AND gate 27 having as its coincidence inputs, a pair of minimum threshold inputs from input comparators 28 and 29, and a clock input on line 30 from clock 31. Write-address counter 26 is connected to the memories 23 and 24 through an address multiplexer 32.

Thus in partial summary, the memories 23 and 24 will always contain the digitized amplitude of the last N events. N is typically 1024, but it may be any positive integer. In any case, effective data persistence is determined by the number of storage locations N rather than time. When a quick response is required, as in the case where a machine parameter of the cell analyzer 10 is being adjusted, N is made small; for example, 64 locations. If a low data rate is anticipated, then N is made large; for example 1024 locations to permit visualization. All this permits evaluation of any populations present. In the event data stops entirely, the display continues to show the last N points since these are retained by memories 23 and 24.

In order to read-out the digital memories 23 and 24, there is provided a read-address counter 33 driven by clock 31 which through address multiplexer 32 and by the read-input on line 34 addresses the memory location 1 through N and presents the memory contents to a pair of X-Y digital to analog converters (DACs) 36 and 37. These drive the X and Y deflection circuits 13 and 12 respectively. This is done independently of the writing process. In addition, read line 34, through a delay unit 38 drives the Z unblanking line 14. The read-address counter 33 is advanced sequentially by the fixed frequency clock 31 at a rate consistent with the CRT phosphor persistence to generate a population display based on the last N data points. This display will be updated by new events as they occur, but will always contain the last N data points. In the event the data stops entirely, the display continues of course to show the last N points, but without any activity or changes.

As discussed above, new data overrides old data in the same sequence in which the old data was originally stored. This has the effect of erasing the oldest point in time and storing a new data point at that location. Thus the oldest data will disappear as new data is acquired at whatever the acquisition rate is. Thus, this in effect is a variable persistence feature. However the persistence is in terms of the number of storage locations selected and the data rate rather than in terms of time.

If the same or a substantially identical X-Y data pair is collected several times, that point will of course be stored at several locations in the memory at the same time. Therefore, it will be written during the scan of the cathode ray tube several times and will provide an increased brightness for that particular point. Thus, in actuality, a three-axis display is provided; that is X and Y corresponding to the data acquisition pairs, and a Z intensity display corresponding to the number of elements at each X-Y coordinate because of the multiple write feature. This gives a display which reveals the relative abundance of subpopulations of cells.

In summary, the advantages of this system include the use of a conventional low-cost CRT, the ability to store and display data for an indefinite time, and a persistence effect which is linked to the data rate, and the number of storage locations selected, not to an independent time parameter. Since data is stored in digital form, other data types such as alpha-numeric characters and markers may be handled and displayed on the same CRT as the data. Because marker location data is handled by the same process as the location of data, such marker positions are automatically correctly registered with respect to the data points. The system may be implemented as described with hardware, or by means of a mini or micro computer system.

It is claimed as follows:

1. Apparatus for displaying on a conventional cathode ray tube (CRT) with X-Y deflection circuits two parameters of populations of particles where said particles are being analyzed and/or sorted by apparatus which provides for each particle a pair of substantially concurrent analog signals representative of two properties of each particle of said populations comprising;
    analog-to-digital converter means for converting each of said analog signals to a digital number;
    a pair of digital storage means each with a predetermined amount of addressable storage locations for sequentially storing said digital numbers;
    means for overwriting, in the sequence in which stored, previously stored digital numbers when said storage is exceeded;
    means for reading said pair of storage means, including a pair of digital-to-analog converters for respectively receiving said stored digital numbers and driving the X-Y deflection circuits of said CRT; and including means for unblanking said CRT.

2. Apparatus as in claim 1 where substantially identical digital number pairs may be concurrently stored in said digital storage means whereby a displayed X-Y point on said CRT for such identical numbers is brighter than other points.

3. Apparatus as in claim 1 where said analog signals include markers, designating regions of interest, said storage means storing such markers in the same manner as said pair of analog signals.

4. Apparatus as in claim 1 where said concurrent analog signals are being produced at a predetermined data rate, and whereby the effective persistence of said conventional CRT is a function of said predetermined number of addressable storage locations and said data rate.

* * * * *